US006933278B1

(12) United States Patent  
Vickers et al.

(10) Patent No.: US 6,933,278 B1
(45) Date of Patent: Aug. 23, 2005

(54) TREATMENT OF HYPERTENSION USING GROWTH HORMONE IN MAMMALS SUBJECTED TO FETAL PROGRAMMING

(75) Inventors: Mark H. Vickers, Auckland (NZ); Bernhard H. H. Breier, Auckland (NZ); Betina A. Ikenasio, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 0 days.

(21) Appl. No.: 09/856,704

(22) PCT Filed: Nov. 26, 1999

(86) PCT No.: PCT/NZ99/00198

§ 371 (c)(1),
(2), (4) Date: Jul. 18, 2001

(87) PCT Pub. No.: WO00/30588

PCT Pub. Date: Jun. 2, 2000

(30) Foreign Application Priority Data

Nov. 26, 1998 (NZ) ................................................ 333035

(51) Int. Cl.$^7$ ........................ A61K 38/00; A61K 38/27; C07K 14/61
(52) U.S. Cl. ........................ 514/12; 530/399; 530/351; 424/92; 424/569
(58) Field of Search ................................ 530/357, 399; 514/12, 2; 424/9.2, 569, 198.1

(56) References Cited

FOREIGN PATENT DOCUMENTS

WO        97/38709        10/1997

OTHER PUBLICATIONS

Baker, D.J. P., Outcome of low birthweight (1994), Hormone Research 42:223–230.*
Job et al., Follow–up of three years of treatment with growth hormone and of one post–treatment year, in children with severe growth retardation of intrauterine onset (1996), Pediatric Research 39: 354–359.*
Gudmundur, Johannsson, "Growth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, (1997).
Rosen, Thord, "Cardiovascular Risk Factors in Adult Patients with Growth Hormone Deficiency", Acta Endocrinologica, 1993, 129; 195–200.

Jorgensen, Jens O.L., "Adult Growth Hormone Deficiency", Horm. Res. 1994; 42:235–241.
Salomon, Franco, "The Effects of Treatment With Recombinant Human Growth Hormone on Body Composition and Metabolism in Adults with Growth Hormone Deficiency", The New England Journal of Medicine, vol. 321, No. 26: 1797–1803, Dec. 28, 1989.
Lopez–Velasco, Rasario, "Cardiac Involvement in Acromegaly: Specific Myocardiopathy or Consequence of Systemic Hypertension", Journal of Clinical Endocrinology and Metabolism, vol. 82, No. 4, 1047–1053, (1997).
Sas, Theo, "Body Composition, Blood Pressure, Lipid Metabolism before and during Long–Term Grwoth Hormone (GH) Treatment in Children with Short Stature Born Small for Gestational Age Either with or without GH Deficiency", Journal of Clinical Endocrinology and Metabolism, vol. 85, No. 10: 3786–3792, (2000).
Coves, Maria J., Clinical Note–Antihypertension Therapy with Guanfacine Induces Elevated Plasma Growth Hormone Levels In Diabetic Patients, Journal of Medicine, vol. 20, Nos. 3 & 4, 1989, 291–297, (1989).
Bengtsson, B.A., "Untreated Growth Hormone Deficiency Explains Premature Mortality in Patients with Hypopituitarism", Growth Hormone and IGF Resarch, 1998, 8 (Suppl. A), 77–80.
Salomon et al, "The Effects of Treatment . . . ," The New England Journal of Medicine, vol. 321, No. 26 pp. 1797–1803 (1989).
Rosen et al, "Cardiovascular risk factors . . . ," Acta Endocrinologica, vol. 129, pp. 195–200 (1993).

* cited by examiner

*Primary Examiner*—Janet Andres
*Assistant Examiner*—Jegatheesan Seharaseyon
(74) *Attorney, Agent, or Firm*—Fliesler Meyer LLP

(57) ABSTRACT

Embodiments of this invention include methods for decreasing hypertension in mammals subjected to adverse cardiovascular fetal programming or a long-term adverse postnatal environment. Fetal programming can result from adverse intrauterine conditions, including growth retardation or undernutrition. Adverse postnatal environments include either hypocaloric or hypercaloric nutrition. Decreasing hypertension is such mammals can be accomplished by administering an agent that increases the effective amount of a growth hormone. Such agents can include a growth hormone, an agent that increases the effective concentration of a growth hormone in the mammal, or an agent that decreases inhibition of a growth hormone's effects. Such agents can be used either alone, or in combination with other anti-hypertensive agents.

17 Claims, 2 Drawing Sheets

US 6,933,278 B1

TREATMENT OF HYPERTENSION USING GROWTH HORMONE IN MAMMALS SUBJECTED TO FETAL PROGRAMMING

FIELD OF THE INVENTION

This invention relates to the treatment of hypertension, and more particularly to the treatment of hypertension in individuals following intrauterine programming of cardiovascular pathophysiology.

BACKGROUND

It is known that disordered fetal growth which is caused by many events including maternal undernutrition during pregnancy, as well as having immediate effects on the fetus, may have long term health consequences for individuals (Barker, D. J. Outcome of low birthweight, *Hormone Research* 42:223–230, 1994; Barker, D. J. Growth in utero and coronary heart disease, *Nutr. Rev.*, 52:S1–S7, 1996). In particular, it has become evident that in addition to the well recognised long term sequelae of persistent growth failure, disordered fetal growth is associated with a higher incidence of hypertension, cardiovascular, cerebrovascular and metabolic disorders in adulthood. (Barker, D. J. Outcome of low birthweight, *Hormone Research* 42:223–230, 1994; Barker, D. J. Growth in utero and coronary heart disease, *Nutr. Rev.*, 52:S1–S7, 1996; Woodall, S. M., et al., Chronic Maternal Undernutrition in the Rat Leads to Delayed Postnatal Growth and Elevated Blood Pressure in Offspring, *Pediatr. Res.* 40: 438–443, 1996).

Hypertension, or high blood pressure, is a particularly significant problem in the adult population. This is because it is common, its consequences are far reaching and can be devastating and the symptoms do not show until late in its course, High blood pressure is one of the major risk factors for coronary heart disease and strokes. It can also lead to congestive heart failure, aortic dissection, and renal failure. Over half of patients with angina pectoris, sudden death, stroke, and atherothrombotic occlusion of the abdominal aorta or its branches have hypertension. Greater than 70% of people with dissecting aortic aneurysm, intracerbral haemorrhage, or rupture of the mycoardial wall have high blood pressure. It is a major risk factor for atherosclerosis. Treatment of high blood pressure can prolong life. Screening programmes reveal that 25% of the general population are hypertensive (Schoen, F. J. (1994). Blood Vessels. In Robbins Pathologic Basis of Disease. Edited by R. S. Cotran, V. Kumar, and F. J. Schoen. Philadelphia: W. B. Saunders Company. 467–516). The prevalence of high blood pressure increases with age. However, in older age groups the disease is usually relatively mild compared to that in young adults where it is often more sever. Approximately 90 to 95% of hypertension is idiopathic and of the remaining 5 to 10%, most is secondary to renal disease. Both primary and secondary hypertension may be either benign or malignant.

In the majority of cases, hypertension remains at a modest level and fairly stable from years to decades. However, if the raised blood pressure is not controlled by anti-hypertensive agents, it frequently causes disability and death from heart failure, and substantially increases the risk of myocardial infarction and strokes. Approximately 5% of people have malignant hypertension where blood pressure rapidly increases and if left untreated, leads to death in one to two years.

Recognising the significance of the problem, it is an object of the present invention to provide a method of treating hypertension, in at least a subset of the population (individuals which experienced intrauterine undernutrition or growth retardation or an adverse postnatal environment), or at least to offer the public a useful choice.

SUMMARY OF THE INVENTION

Accordingly, in a first aspect the present invention provides a method of treating hypertension in a mammal, which has experienced intrauterine under nutrition and/or growth retardation or an adverse post-natal environment, the method comprising the step of administering to the mammal an effective amount of an agent, wherein the agent is a ligand which binds to, and activates, the growth hormone receptor.

In another aspect, the present invention provides a method of treating hypertension in a mammal, which has experienced intrauterine under nutrition and/or growth retardation or an adverse post-natal environment, the method comprising the step of administering to the mammal an effective amount of growth hormone, an analog thereof, or a functionally equivalent ligand.

Generally, the hypertensive state of the mammal will be the result of intrauterine fetal programming, or of an unfavorable/adverse postnatal environment (eg. a hypercaloric diet). However, any mammal with hypertension can be treated in accordance with the above methods.

Preferably, the mammal to be treated is an adult mammal.

As used herein, the term "intrauterine undernutrition or growth retardation" means disordered fetal growth with causes which include maternal undernutrition, placental insufficiency, endocrine abnormalities and substance abuse, as evidenced by a relatively low birth weight.

As used herein, "analog" means a protein which is a variant of growth hormone through insertion, deletion or substitution of one or more amino acids but which retains at least substantial functional equivalency.

The term "functionally equivalent ligand" means an agent which binds to and activates the receptors which growth hormone binds to and activates to give the anti-hypertensive effect.

In a further aspect, the invention provides a method of treating hypertension in a mammal, which has experienced intrauterine under nutrition and/or growth retardation or an adverse post-natal environment, the method comprising the step of increasing the effective concentration of growth hormone, an analog thereof or a functionally equivalent ligand in the mammal.

The method is particularly suitable for treating a mammal which has experienced either an adverse fetal environment, an adverse postnatal environment, or both.

Preferably, the effective concentration of said growth hormone analog or ligand is increased through direct administration.

Preferably, the effective concentration of growth hormone is increased through direct administration of growth hormone.

Alternatively, the effective concentration of growth hormone is increased through administration of an agent which either stimulates production of growth hormone or which lessens or prevents inhibition of growth hormone activity.

Preferably, the mammal is an adult human.

In a further aspect, the present invention provides the use of an agent selected from growth hormone, an analog thereof or a functionally equivalent ligand in the preparation of a medicament for treating hypertension in a mammal, which has experienced intrauterine under nutrition and/or growth retardation or an adverse post-natal environment.

In yet a further aspect, the invention provides the use, in the preparation of a medicament for treating hypertension in a mammal, which has experienced intrauterine under nutrition and/or growth retardation or an adverse post-natal environment, of an agent which either stimulates production of growth hormone or which lessons or prevents inhibition of growth hormone activity.

Although the invention is broadly as defined above, it also includes embodiments of which the following description provides examples.

BRIEF DESCRIPTION OF THE DRAWINGS

In particular, the invention will be better understood with reference to the accompanying drawings, in which.

DESCRIPTION OF THE INVENTION

Figure 1:
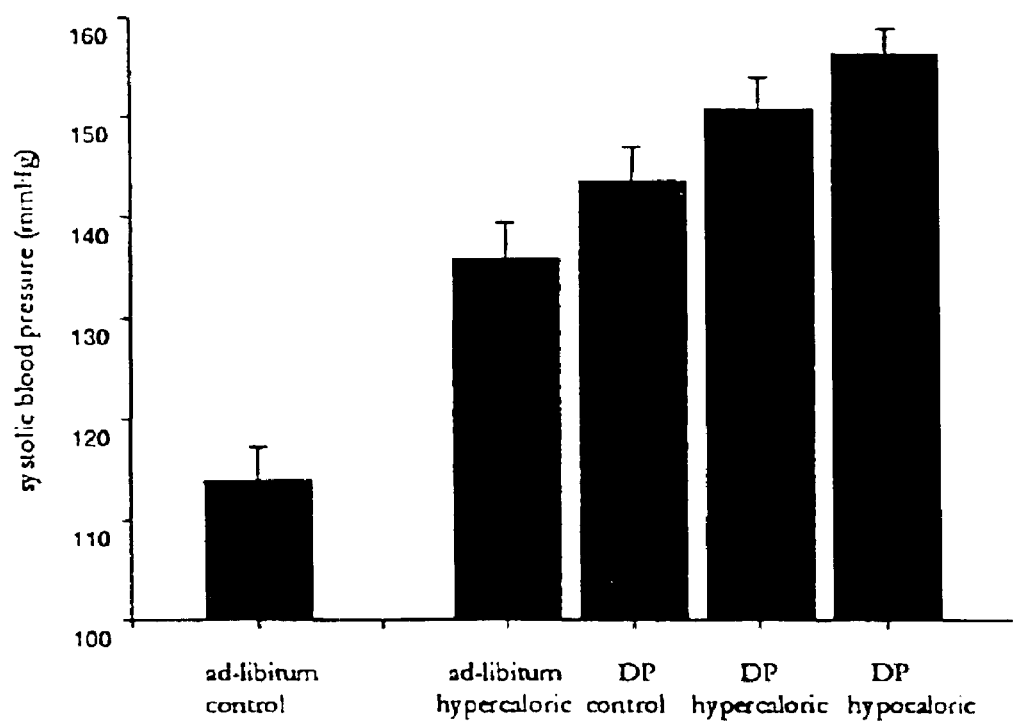
FIG. 1 shows the mean systolic blood pressure in *ad-libitum* and developmentally programmed (DP) rat offspring. The data is mean ±SEM with a minimum of 5 animals per group.

The focus of the invention is on the treatment of hypertension. It is particularly on the treatment of hypertension in a subset of the adult population. The applicant's surprising finding, which underlies the present invention, is that administration of growth hormone to an adult mammal with hypertension can reduce systolic blood pressure. This is particularly true for mammals which have been subject as a fetus to adverse cardiovascular programming during pregnancy or which have undergone intrauterine growth retardation (IUGR), and have therefore been "programmed" to subsequently develop hypertension.

This finding with respect to growth hormone is unexpected given the previous reports associating an increase in systolic blood pressure with long-term exposure to endogenous growth hormone in acromegalics (Sacca. L., et al., Growth Hormone and the Heart Endocrine Reviews, Vol 15, No. 5, 555–573 [1994]) and low systolic blood pressure after a long-term lack of exposure to endogenous growth hormone in growth hormone deficient adults (Sacca, L., et al., Growth Hormone and the Heart. Endocrine Reviews, Vol 15, No. 5, 555–573 [1994]). In other studies, growth hormone has been reported to decrease diastolic blood pressure (Johannsson, G., et al., Growth hormone treatment of abdominally obese men reduces abdominal fat mass, improves glucose and lipoprotein metabolism and reduces diastolic blood pressure. *Journal of Clinical Endocrinology and Metabolism*, Vol 82, No. 3 727–734 (1997)), while having no effect on systolic pressure.

The invention therefore provides a method of treating hypertension in a mammal, such as a mammal which has experienced intrauterine growth retardation or undernutrition or which has experienced a long term adverse postnatal environment such as hypocaloric or hypercaloric nutrition. It is however envisaged that the invention will have application in treating mammalian hypertension caused by other aetiologies, risk factors and environmental effects.

It is also envisaged that the principal application of the method of the invention will be to adult humans although treatment of pre-adult and non-human mammals is in no way excluded.

In a preferred aspect, the method of the present invention involves administering to the mammal an effective amount of growth hormone, an analog thereof or a functionally equivalent ligand. In a preferred embodiment, growth hormone itself is administered to the mammal.

The growth hormone can be any mammalian growth hormone, with examples being human growth hormone, bovine growth hormone, rat growth hormone and porcine growth hormone. It is however preferred that the growth hormone employed be human growth hormone where the mammal is a human.

The growth hormone which is used in this invention can be obtained from any commercial source.

In addition to growth hormone itself, the use of analogs of growth hormone or functionally equivalent ligands of growth hormone is contemplated.

A protein is a functional equivalent of another protein for a specific function if the equivalent protein is immunologically cross-reactive with, and has at least substantially the same function as, the original protein. The equivalent can be, for example, a fragment of the protein, a fusion of the protein with another protein or carrier, or a fusion of a fragment with additional amino acids. For example, it is possible to substitute amino acids in a sequence with equivalent amino acids using conventional techniques. Groups of amino acids normally held to be equivalent are:

(a) Ala, Ser, Thr, Pro, Gly;
(b) Asn, Asp, Glu, Gln;
(c) His, Arg, Lys;
(d) Met, Leu, Ile, Val; and
(e) Phe, Tyr, Trp.

It will also be appreciated that the present invention also extends to the administration of an agent which either stimulates production of growth hormone, or which lessens or prevents inhibition of growth hormone activity, ie to the administration of growth hormone agonists or secretagogues (substances which effect a direct increase in production of growth hormone).

Examples of agents which stimulate growth hormone and production or lessen or prevent its inhibition include growth hormone releasing peptides (GHRP) such as GHRP-1, GHRP-2, GHRP-6, hexarelin, G-7039, G-7502, L-692,429, L-692,585, L-163,191 or growth hormone releasing hormone (GHRH) or inhibitors of growth hormone antagonists (substances which bind growth hormone or otherwise prevent or reduce the action of growth homone within the body). These latter compounds exert an indirect effect on effective growth hormone concentrations through the removal of an inhibitory mechanism, and include substances such as somatostatin release inhibitory factor (SRIF).

The active agent can be administered using any suitable route. Where growth hormone is the active compound to be administered, it will generally be administered as an injectable formulation, in combination with one or more suitable carriers or excipients. Those persons skilled in the art will appreciate how suitable formulations can be prepared.

The active agent can also be administered in combination. For example, a combination of growth hormone and other conventional anti-hypertensive agent(s), for example ACE (angiotensin-converting enzyme) inhibitors such as quinapril, is also contemplated.

Another possibility is administration of a replicable vehicle encoding the growth hormone/analog/ligand to the patient. Such a vehicle (which may be a modified cell line or virus which expresses growth hormone/analog/ligand within the patient) could have application in increasing the concentration of the active compound within the patient for a prolonged period. Such a vehicle could well form part of an implant.

Dosage levels will be formulation dependent. However, by way of example, the recommended dosage rate of growth hormone formulated for injection would be in the range of 0.1 ug/kg/day to 1 mg/kg/day. A preferred rate would be from approximately 2 to 200 ug/kg/day.

The invention will now be further described with reference to the following non-limiting examples.

EXAMPLES

Experimental

Virgin Wistar rats (age 100±5 days, n=15 per group) were time mated using a rat oestrous cycle monitor (Fine Science Tools INC., North Vancouver, BC, Canada) to assess the stage of oestrous of the animals prior to introducing the male. Day 1 of pregnancy was determined by the presence of spermatozoa after a vaginal smear. After confirmation of mating, rats were housed individually in standard rat cages containing wood shavings as bedding and with free access to water. All rats were kept in the same room with a constant temperature maintained at 25° c. and a 12-h light: 12-h darkness cycle. Dams were randomly assigned to receive food either *ad-libitum* (n=30, 15 study animals and 15 dams for crossfostering) or to receive 30% of *ad-libitum* (determined by measuring food intake on the previous day of an *ad-libitum* fed dam). The diet composition was protein 18%, fat 4%, fibre 3%, ash 7% and carbohydrate 58% (Diet 86, Skellerup Stock Foods, Auckland, New Zealand). Food intake and body weights were recorded daily.

Following birth, offspring from restricted fed dams were crossfostered onto *ad-libitum* fed mothers. Crossfostering is necessary due to lactational insufficiency in restricted fed dams. Litter size was adjusted to 8 pups per litter. Preweaning weights of all pups were recorded daily. At weaning (age 21 days) pups were sexed and housed in cages (males 2per cage, females 3 per cage) and fed on of three diets regimes (normal, hypercaloric and hypocaloric (705 of normal) *ad libitum* for the remainder of the study. At 90±5d (corresponding to adulthood), systolic blood pressure recordings were taken (n=12 per group).

Treatment was then commenced for 21 days with recombinant bovine growth hormone (rbGH) at a dose of 10 ug/g/day given over 2 subcutaneous injections (8 am and 5 pm). Control animals were treated with carbonate buffered saline (CBS, pH 9.4) using an identical protocol. Immediately prior to sacrifice (24–48 hrs), a repeated systolic blood pressure recording was taken using identical conditions (method is outlined below).

Normal and Hypercaloric Diets

Two custom made diets were prepared for the study. The composition of the diets was as follows:

Control diet: protein 19.4%, fat 5%, fibre 5%, salt 1.5%, 2959 kcal/kg

Hypercaloric diet: protein 30%, fat 30%, fibre 5%, salt 1.5%, 4846 kcal/kg

Both diets had a protein/energy ratio of 26%. Hypocalorically fed animals were given 70% of the intake of the DP control fed animals.

Methods

Systolic blood pressures were recorded by tail cuff plethysmorgraphy according to the manufacture's instructions (Blood pressure analyser IITC, Life Science, Woodland Hills, Calif., USA). Rats were restrained in a clear plastic tube in a heated room (25–28° C.). After the rats had acclimatised (10–15 min) the cuff was placed on the tail and inflated to 240 mmHg. Pulses were recorded during deflation at a rate of 3 mmHg/sec and reappearance of a pulse was used to determine systolic blood pressure. A minimum of 3 clear systolic blood pressure recordings were taken per animal. Coefficient of variation for repeated measurements was <5%.

Results

Prior to onset of growth hormone therapy, developmentally programmed (DP) offspring showed a marked degree of hypertension as compared to *ad-libitum* offspring on a control die (p<0.001). Systolic blood pressure in DP offspring was further exacerbated by exposure to either a hypercaloric or hypocaloric diet postnatally (p<0.001, FIG. 1).

Figure 2:
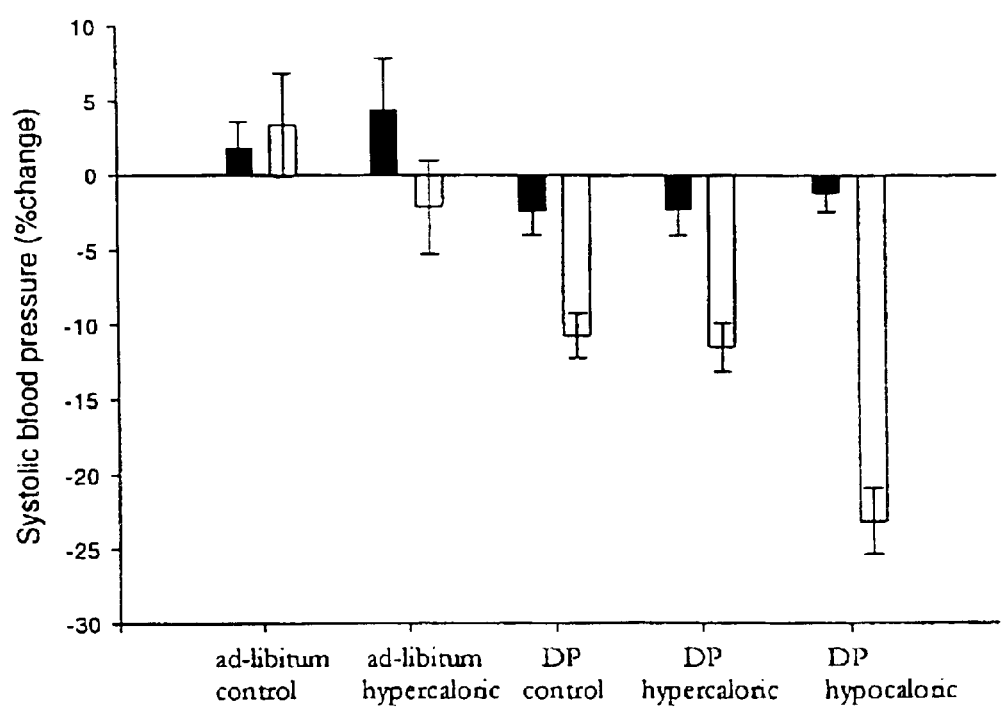
FIG. 2 shows the percent change in systolic blood pressure in the rats following rbGH treatment for 21 days. The data is mean ±SEM, minimum of 5 animals per group.

Systolic blood pressure was significantly decreased in all DP animals treated with rbGH for 21 days (FIG. 2). Although *ad-libitum* animals on a hypercaloric diet showed a significant increase in systolic blood pressure prior to treatment, growth hormone therapy did not reduce the degree of hypertension observed in these animals. Similarly, offspring from *ad-libitum* control fed mothers showed no significant change in systolic blood pressure following treatment. The reduction in systolic blood pressure was most marked in the DP animals fed hypocalorically. *Ad-libitum* and DP offspring treated with vehicle only showed no significant change in systolic blood pressure.

Conclusion

The above results clearly demonstrate the efficacy of growth hormone treatment in reducing systolic blood pressure in hypertensive animals whose hypertension is either caused by fetal programming or by an adverse postnatal environmental effect such as hypercaloric or hypocaloric nutrition. The very surprising finding of this example is that growth hormone did not reduce blood pressure in the normal control animals.

There are no examples in the literature where growth hormone has caused such a profound fall in systolic blood pressure in a hypertensive animal. Therefore the mechanisms of this effect either by effects on peripheral resistance of by direct action on the heart are unknown. The almost complete normalization of systolic blood pressure in these hypertensive animals is also a surprise.

INDUSTRIAL APPLICATION

Hypertension is a multi-faceted health problem of aging, genetics, and, particularly, lifestyle. For example, the combination of post-natal diet and undernutrition causes health problems in terms of high blood pressure. However, the combination of undernutrition or another fetal insult plus cigarette smoking also causes hypertension. Therefore the "programming" plus a post-natal insult (such as hypercaloric or hypocaloric diet) will cause hypertension.

It is believed that the method of the present invention will be effective in treating hypertension, particularly in offspring following fetal intrauterine undernutrition or growth retardation during pregnancy. The possibility of effective hormonal therapy for the hypertensive population is of immense public health significance.

Although the invention has been described with reference to a particular embodiment, it will be appreciated by those persons skilled in the art that variations and modifications may be made without departing from the spirit and scope of the invention.

What is claimed is:

1. A method of treating hypertension in a mammal, comprising administering to the mammal an amount of growth hormone sufficient to reduce systolic blood pressure, wherein said mammal has a history of one or more of the following: low birth weight, intrauterine undernutrition, growth retardation, hypercaloric diet, hypocaloric diet, placental insufficiency or substance abuse; wherein said mammal does not have a growth hormone deficiency.

2. The method as claimed in claim 1, wherein the mammal is an adult mammal.

3. The method as claimed claim 2, wherein the mammals is an adult human.

4. The method as claimed in claim 3 wherein the said growth hormone is human growth hormone.

5. The method as claimed in claim 1 wherein the growth hormone is administered to the mammal in combination with a second anti-hypertensive agent.

6. The method of claim 5, wherein the said second anti-hypertensive agent is an angiotensin-converting enzyme inhibitor.

7. The method of claim 6, wherein said angiotensin-converting enzyme inhibitor is quinapril.

8. A method of treating hypertension in a mammal, which has a history of one or more of the following: low birth weight, intrauterine undernutrition, growth retardation, hypercaloric diet, hypocaloric diet, placental insufficiency or substance abuse; wherein said mammal does not have a growth hormone deficiency, comprising increasing the effective cosentration of growth hormone in the mammal, sufficient to decrease systolic blood pressure.

9. The method as claim 8, wherein the mammal has a history of hypocaloric or hypercaloric diet.

10. The method of claim 8, wherein the effective concentration of the growth hormone, is increased through administration of an agent which either stimulates production of growth hormone or which lessens or prevents inhibition of growth hormone activity.

11. The method as claimed in claim 8, wherein the mammal is an adult human.

12. The method of claim 8, wherein the said step of increasing the effective concentration of growth hormone is carried out by administering a growth hormone releasing peptide (GHRP).

13. The method of claim 8, wherein said GHRP is selected from the group consisting of GHRP-1, GHRP-2, GHRP-6, hexareline, G-7039, G7502, L-692,429, L-692,585 and L-163,191.

14. The method of claim 8, wherein the said step of increasing the effective concentration of growth hormone is carried out by administering a growth hormone releasing hormone (GHRH).

15. The method of claim 8, wherein the said step of increasing the effective concentration of growth hormone is carried out by administering an inhibitor of a growth hormone antagonist.

16. The method of claim 15, wherein the said inhibitor of a growth hormone antagonist is somatostatin release inhibitor factor.

17. The method of claim 1, wherein the dose of said growth hormone is in the range of:

about 0.1 $\mu$g/kg/day to about 1 mg/kg/day.

* * * * *